(12) United States Patent
Lim et al.

(10) Patent No.: US 9,133,156 B2
(45) Date of Patent: Sep. 15, 2015

(54) METHOD FOR PREPARING SELENYL-SUBSTITUTED AROMATIC ALDEHYDE COMPOUNDS

(75) Inventors: Dongyeol Lim, Seoul (KR); Do-Hyun Nam, Seoul (KR); Rashmi Dubey, Seoul (KR)

(73) Assignees: Sejong University Industry Academy Cooperation Foundation, Seoul (KR); Samsung Life Public Welfare Foundation, Seoul (KR)

( * ) Notice: Subject to any disclaimer, the term of this patent is extended or adjusted under 35 U.S.C. 154(b) by 33 days.

(21) Appl. No.: 13/543,288

(22) Filed: Jul. 6, 2012

(65) Prior Publication Data

US 2014/0012021 A1    Jan. 9, 2014

(51) Int. Cl.
*C07D 213/80* (2006.01)
*C07D 317/62* (2006.01)
*C07C 391/02* (2006.01)

(52) U.S. Cl.
CPC ............ *C07D 317/62* (2013.01); *C07C 391/02* (2013.01)

(58) Field of Classification Search
CPC .................................................... C07D 317/62
USPC ........................................................ 546/298
See application file for complete search history.

(56) References Cited

FOREIGN PATENT DOCUMENTS

| JP | 57-070883 | 1/1982 |
| JP | 60-070193 | 4/1985 |
| KR | 10-2009-0074248 | 6/2009 |
| WO | 2006/077888 | 7/2006 |
| WO | WO/2011/017837 | * 2/2011 |

OTHER PUBLICATIONS

Christiaens et al., Bullerin des Societes Chimques Belges (1970), vol. 79(1-2), pp. 133-141.*
Ruwet etal., Bullerin des Societes Chimques Belges (1969), vol. 78(9-10), pp. 571-582.*
Pirson et al., Bullerin des Societes Chimque de France (1973), vol. 2(pt. 2), pp. 704-707.*
Gillissen et al., J. Org. Chem. (1980), vol. 45(2), pp. 319-328.*
Syper et al., Tetrahed. (1988), vol. 44(19), pp. 6119-6130.*
Garnovskii et al., Doklady Akademii Nauk SSSR (1989), vol. 306(4), pp. 872-875.*
Dari et al., Heterocycles (1992), vol. 34(9), pp. 1737-1748.*
Lin et al., Tetrahed. Letrs. (2006), vol. 47(12), pp. 1941-1944.*
Jalbout et al., J. Organomet. Chem. (2007), vol. 692(5), pp. 1039-1047.*
Lin et al., Tetrahed. (2007), vol. 63(13), pp. 2787-2797.*
Shirani et al., Organomet. (2008), vol. 27(15), pp. 3960-3963.*
Wang et al., Adv. Synthes. and Catalys. (2009), vol. 351(10), pp. 1586-1594.*
Dissendruck et al., Inorg. Chem. (2009), vol. 48(22), pp. 10819-10825.*
Shirani et al., Tetrahed. (2009), vol. 65(40), pp. 8350-8353.*
Panda et al., Dalton Transac. (2011), 40(25), 6684-6690.*
King, Med. Chem., Principle and Practice (1994), pp. 206-208.*

* cited by examiner

*Primary Examiner* — Taofiq A Solola
(74) *Attorney, Agent, or Firm* — Greer, Burns & Crain, Ltd.

(57) ABSTRACT

The present disclosure relates to a novel method for preparing selenyl-substituted aromatic aldehyde compounds by forming a selenolate nucleophile and performing a nucleophilic substitution reaction between the selenolate nucleophile and an aromatic aldehyde starting material.

1 Claim, No Drawings

METHOD FOR PREPARING SELENYL-SUBSTITUTED AROMATIC ALDEHYDE COMPOUNDS

FIELD OF THE INVENTION

The present disclosure relates to a novel method for preparing selenyl-substituted aromatic aldehyde compounds by forming a selenolate nucleophile and performing a nucleophilic substitution reaction between the selenolate nucleophile and an aromatic aldehyde starting material.

BACKGROUND OF THE INVENTION

Recently, Chalcogen chemistry has attracted great attention in the field of organic chemistry. In particular, a biological activity of selenium (Se) has been at the center of attention. Since ebselene(2-phenylbenzisoselenazol-3(2H)-one as a nontoxic glutathione peroxide analogue was synthesized first, considerable efforts have been made to develop stable organic selenium compounds.

Of the organic selenium compounds, a selenyl-substituted aromatic aldehyde compound can serve as an intermediate for synthesizing benzoselenophenes having various biological activities. The selenyl-substituted aromatic aldehyde compound can be obtained by performing a nucleophilic substitution reaction between a selenolate nucleophile as represented by A-Se⁻ and an aromatic aldehyde starting material. At this time, the selenolate nucleophile can be formed by reducing a Se—Se bond of a diselenide compound as represented by general formula A-Se—Se-A.

Reduction of the Se—Se bond of the diselenide compound to form the selenolate nucleophile can be achieved based on several reducing agents such as $NaBH_4$ and $LiEt_3BH$. Further, metals such as indium, lanthanum, and samarium and salts thereof can be used for reducing the Se—Se bond of the diselenide compound. However, it is difficult to obtain the selenyl-substituted aromatic aldehyde compound by the above-described conventional methods. That is because according to the conventional methods, a free aldehyde group of the aromatic aldehyde starting material may be reduced or converted into another functional group at the same time when the Se—Se bond of the diselenide compound is reduced. Meanwhile, some catalytic processes may be applied to the reduction of the Se—Se bond of the diselenide compound, but most of these catalytic processes need to be carried out under harsh reaction conditions.

SUMMARY

The present disclosure provides a novel method for preparing selenyl-substituted aromatic aldehyde compounds with a high yield by using a selenolate nucleophile as represented by A-Se⁻. The novel method can solve a problem that a free aldehyde group of an aromatic aldehyde starting material is reduced or converted into another functional group at the same time when a Se—Se bond of a diselenide compound is reduced to form the selenolate nucleophile.

To be specific, the present disclosure provides a novel method for preparing selenyl-substituted aromatic aldehyde compounds, the novel method including: forming a selenolate nucleophile as represented by A-Se⁻ by reducing a diselenide compound as represented by general formula A-Se—Se-A with a material containing a thiol group as a reducing agent; and performing a nucleophilic substitution reaction between the selenolate nucleophile and an aromatic aldehyde starting material.

In accordance with a first aspect of the present disclosure, there is provided a method for preparing a selenyl-substituted aromatic aldehyde compound as represented by Formula 2, the method comprising: preparing a reaction mixture including a diselenide compound as represented by general formula A-Se—Se-A, a solvent, and a reducing agent; and adding an aromatic aldehyde starting material as represented by Formula 1 and a base to the reaction mixture and reacting thereof:

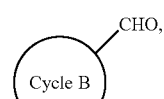
[Formula 1]

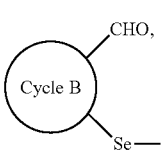
[Formula 2]

wherein A is a substitutable $C_{1-10}$-alkyl group, a substitutable $C_{1-10}$-alkoxycarbonyl-$C_{1-10}$-alkyl group, a substitutable allyl group, a substitutable aromatic cyclic group, a substitutable aromatic cyclic group substituted by one or two of a $C_{1-10}$-alkyl group, a substitutable aromatic cyclic group substituted by a halo group, or a substitutable aromatic cyclic group substituted by a nitro group; the cycle B includes one or more of functional groups $R_1$ to $R_4$; and the cycle B is a 5-membered heterocyclic ring or aromatic ring, a 6-membered heterocyclic ring or aromatic ring, or a heterocyclic ring or aromatic ring with the 5-membered ring fused to the 6-membered ring; and each of the 5-membered ring and the 6-membered ring includes 5 atoms and 6 atoms each selected from a group consisting of C, N, O, S, and Se; each of the functional groups $R_1$ to $R_4$ is independently hydrogen; an electron donating group selected from a group consisting of an aromatic hydrocarbon group, an amine group, a $C_{1-10}$-alkyl group, a $C_{1-10}$-alkoxy group, and an ether group; or an electron withdrawing group selected from a group consisting of a halo group, a nitro group, a cyano group, and a carbonyl group; and X is a halo group.

In accordance with a second aspect of the present disclosure, there is provided a selenyl-substituted aromatic aldehyde compound as represented by Formula 2:

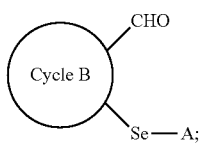
[Formula 2]

wherein A is a substitutable $C_{1-10}$-alkyl group, a substitutable $C_{1-10}$-alkoxycarbonyl-$C_{1-10}$-alkyl group, a substitutable allyl group, a substitutable aromatic cyclic group, a substitutable aromatic cyclic group substituted by one or two of a $C_{1-10}$-alkyl group, a substitutable aromatic cyclic group substituted by a halo group, or a substitutable aromatic cyclic group substituted by a nitro group; the cycle B includes one or more of functional groups $R_1$ to $R_4$; and the cycle B is a 5-membered heterocyclic ring or aromatic ring, a 6-membered heterocyclic ring or aromatic ring, or a heterocyclic ring or aromatic ring with the 5-membered ring fused to the 6-membered ring; and each of the 5-membered ring and the 6-membered ring includes 5 atoms and 6 atoms each selected from a group consisting of C, N, O, S, and Se; and each of the functional groups $R_1$ to $R_4$ is independently hydrogen; an electron donating group selected from a group consisting of an aromatic hydrocarbon group, an amine group, a $C_{1-10}$-alkyl group, a $C_{1-10}$-alkoxy group, and an ether group; or an electron withdrawing group selected from a group consisting of a halo group, a nitro group, a cyano group, and a carbonyl group.

Advantageous Effects of Invention

The present disclosure provides a novel method for preparing selenyl-substituted aromatic aldehyde compounds in accordance with the present disclosure, a free aldehyde group of the aromatic aldehyde starting material is not reduced or converted into another functional group and a Se—Se bond of the diselenide compound is selectively reduced by using a material containing a thiol group as a reducing agent. Therefore, as compared with conventional methods in which $NaBH_4$ or $LiEt_3BH$ is used as a reducing agent, it is possible to remarkably increase a yield of the selenyl-substituted aromatic aldehyde compounds. Further, by using the diselenide compound as represented by general formula A-Se—Se-A as a material for forming the selenolate nucleophile, it is possible to obtain easiness of handling and sufficient reactivity. Furthermore, by adding a base, the reducing agent containing the thiol group can become negatively charged thiolate ($RS^-$) and reducing power can be increased. However the thiolate is more highly reactive with the diselenide compound. In the present disclosure the base is added during a reaction after adding the aromatic aldehyde starting material, and, thus, the thiolate attacks an allyl group of the aromatic aldehyde starting material to selectively perform a nucleophilic substitution reaction. As a result, a yield of a final product can be increased.

In accordance with the present disclosure, in order to increase the yield of the final product, selenyl-substituted aromatic aldehyde compounds, if the aromatic aldehyde starting material contains an electron donating substituent, it is advantageous to use a strong base, whereas if the aromatic aldehyde starting material contains an electron withdrawing substituent, it is advantageous to use a weak base. That is, a kind of a base can be determined depending on a property of a substituent of the aromatic aldehyde starting material and the yield of the final product can be increased accordingly.

The selenyl-substituted aromatic aldehyde compounds obtained with a high yield and least byproduct in accordance with the present disclosure can serve as a useful intermediate for synthesizing benzoselenophenes having various biological activities.

DETAILED DESCRIPTION OF THE INVENTION

Hereinafter, illustrative embodiments and examples will be described in detail so that inventive concept may be readily implemented by those skilled in the art. However, it is to be noted that the present disclosure is not limited to the illustrative embodiments and examples but can be realized in various other ways.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

The terms "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "$C_{1-10}$-alkyl group" may include a linear or branched, saturated or unsaturated alkyl group having a number of carbon atoms of 1 to 10 and including, but not limited to, methyl, ethyl, propyl, butyl, pentyl, hexyl, hepxyl, octyl, nonyl, decyl, or isomers thereof.

Through the whole document, the term "substitutable $C_{1-10}$-alkyl group" may contain a substituent containing, for example, but not limited to, an alkyl group, a hydroxyl group, an alkoxy group, a halo group, a nitril group, or a nitro group; or an allyl group substituted by an alkyl group, a hydroxyl group, an alkoxy group, a halo group, a nitril group, or a nitro group. Further, through the whole document, the term "substitutable $C_{1-10}$-alkyl group" may contain, but is not limited to, a double bond or a triple bond.

Through the whole document, the term "$C_{1-10}$-alkylene group" may include a linear or branched, saturated or unsaturated alkylene group having a number of carbon atoms of 1 to 10 and including, but not limited to, methylene, ethylene, propylene, butylene, pentylene, hexylene, hepxylene, octylene, nonylene, decylene, or isomers thereof.

Through the whole document, the term "$C_{1-10}$-alkoxy group" may include, but is not limited to, an alkoxy group in which the above-defined "$C_{1-10}$-alkyl group" is bonded to an oxygen atom.

Through the whole document, the term "halo group" may include, but is not limited to, F, Cl, Br, or I.

Through the whole document, the term "$C_{1-10}$-alkoxycarbonyl-$C_{1-10}$-alkyl group" may include, but is not limited to, a carbonyl group containing the above-defined "$C_{1-10}$-alkoxy group" and "$C_{1-10}$-alkyl group".

Through the whole document, the term "allyl group" may include, but is not limited to, an allyl group having a number of carbon atoms of 3 to 10, i.e. $C_{3-10}$-allyl group, for example, an allyl group having a number of carbon atoms of 3, 4, 5, 6, 7, 8, 9, or 10.

Through the whole document, the terms "aromatic hydrocarbon group" and "aromatic cyclic group" which can have a substituent each may include, but is not limited to, a phenyl group which can have a substituent, a benzyl group which can have a substituent, a toluoyl group which can have a substituent, a styrenyl group which can have a substituent, or a naphthalene group which can have a substituent.

Through the whole document, the term "heterocyclic group" may have the same meaning as "heterocyclic ring" typically used in the art and may include, but is not limited to, a ring-shaped organic compound containing carbon and other atoms such as nitrogen, oxygen, sulfur, phosphorus, or silicon as an atom constituting the ring.

Through the whole document, the term "5-membered ring" may include a cyclic group containing five atoms which can have a substituent on a backbone of a ring, and for example, "5-membered heterocyclic ring" may include, but is not limited to, a substitutable heterocyclic group containing five atoms selected from various atoms such as carbon, nitrogen, oxygen, sulfur, and selenium as atoms constituting a backbone of a ring, and for example, "5-membered aromatic ring"

may include, but is not limited to, a substitutable aromatic group containing five carbon atoms as atoms constituting a backbone of a ring.

Through the whole document, the term "6-membered ring" may include a cyclic group containing six atoms which can have a substituent on a backbone of a ring, and for example, "6-membered heterocyclic ring" may include, but is not limited to, a substitutable heterocyclic group containing six atoms selected from various atoms such as carbon, nitrogen, oxygen, sulfur, and selenium as atoms constituting a backbone of a ring, and for example, "6-membered aromatic ring" may include, but is not limited to, a substitutable aromatic group containing six carbon atoms as atoms constituting a backbone of a ring.

Hereinafter, a selenyl-substituted aromatic aldehyde compound and a method of preparing the same in accordance with the present disclosure will be explained in detail with reference to illustrative embodiments and examples, but the present disclosure is not limited thereto.

In accordance with a first aspect of the present disclosure, there is provided a method for preparing a selenyl-substituted aromatic aldehyde compound as represented by Formula 2. The method includes: preparing a reaction mixture comprising including a diselenide compound as represented by general formula A-Se—Se-A, a solvent, and a reducing agent; and adding an aromatic aldehyde starting material as represented by Formula 1 and a base to the reaction mixture and reacting thereof:

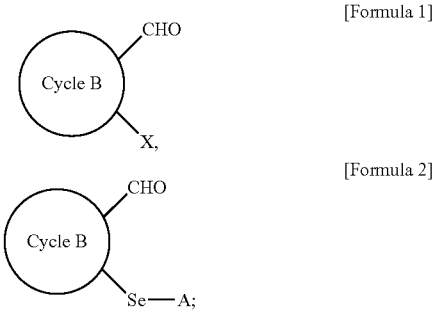

[Formula 1]

[Formula 2]

wherein A is a substitutable $C_{1-10}$-alkyl group, a substitutable $C_{1-10}$-alkoxycarbonyl-$C_{1-10}$-alkyl group, a substitutable allyl group, a substitutable aromatic cyclic group, a substitutable aromatic cyclic group substituted by one or two of a $C_{1-10}$-alkyl group, a substitutable aromatic cyclic group substituted by a halo group, or a substitutable aromatic cyclic group substituted by a nitro group; the cycle B includes one or more of functional groups $R_1$ to $R_4$; and the cycle B is a 5-membered heterocyclic ring or aromatic ring, a 6-membered heterocyclic ring or aromatic ring, or a heterocyclic ring or aromatic ring with the 5-membered ring fused to the 6-membered ring; and each of the 5-membered ring and the 6-membered ring includes 5 atoms and 6 atoms each selected from a group including C, N, O, S, and Se; each of the functional groups $R_1$ to $R_4$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including of a halo group, a nitro group, a cyano group, and a carbonyl group; and X is a halo group.

By way of example, the A may include, but is not limited to, a substitutable $C_{1-10}$-alkyl group, a substitutable $C_{1-10}$-alkoxycarbonyl-$C_{1-10}$-alkyl group, a substitutable $C_{3-10}$-allyl group, a substitutable benzyl group substituted by a $C_{1-10}$-alkyl group, a substitutable benzyl group substituted by a halo group, a substitutable benzyl group substituted by a nitro group, or a substitutable benzyl group.

By way of example, the cycle B may include, but is not limited to, a 5-membered heterocyclic ring, a 5-membered aromatic ring, a 6-membered heterocyclic ring, a 6-membered aromatic ring, a heterocyclic ring with the 5-membered ring fused to the 6-membered ring or an aromatic ring with the 5-membered ring fused to the 6-membered ring, and atoms constituting the respective rings may be substituted by, but not limited to, the functional groups $R_1$ to $R_4$.

By way of example, if the cycle B is a 6-membered heterocyclic ring, the 6-membered heterocyclic ring may contain five carbon atoms which can have a substituent and a nitrogen atom as atoms constituting a ring, and may be represented by, for example, but not limited to, Formula 3 or 4 to be explained hereinafter in an illustrative embodiment.

By way of example, if the cycle B is a heterocyclic ring with the 5-membered ring fused to the 6-membered ring, the 6-membered ring thereof may contain five carbon atoms which can have a substituent and a nitrogen atom as atoms constituting a ring, and the 5-membered ring thereof may contain three carbon atoms which can have a substituent and two oxygen atoms as atoms constituting a ring. The 6-membered ring and the 5-memebered ring may share two carbon atoms with each other, and may be represented by, for example, but not limited to, Formula 5 or 6 to be explained hereinafter in an illustrative embodiment.

By way of example, if the cycle B is a 5-membered heterocyclic ring, the 5-membered heterocyclic ring may contain four carbon atoms which can have a substituent and an oxygen atom, four carbon atoms which can have a substituent and a sulfur atom, or four carbon atoms which can have a substituent and a selenium atom as atoms constituting a ring, and may be represented by, for example, but not limited to, Formula 7 or 8 to be explained hereinafter in an illustrative embodiment.

By way of example, the cycle B does not have to contain all of the functional groups $R_1$ to $R_4$. By way of example, if the cycle B is a 5-membered ring, the 5-membered ring may contain, but is not limited to, $R_1$ to $R_3$, i.e. three functional groups.

In accordance with an illustrative embodiment of the present disclosure, the aromatic aldehyde starting material includes, but is not limited to, a compound as represented by Formula 3, and the selenyl-substituted aromatic aldehyde compound includes, but is not limited to, a compound as represented by Formula 4:

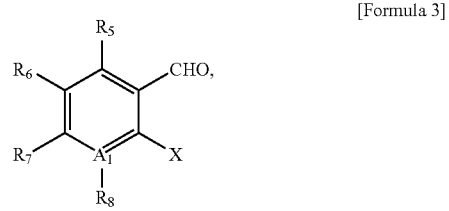

[Formula 3]

[Formula 4]

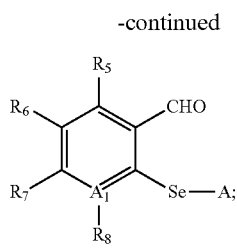

wherein each of the functional groups $R_5$ to $R_8$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including a halo group, a nitro group, a cyano group, and a carbonyl group; $A_1$ is C or N; and A and X are as defined in the first aspect of the present disclosure.

By way of example, the compound as represented by Formula 3 may be, but is not limited to, an example of the compound as represented by Formula 1 of the first aspect of the present disclosure, and the compound as represented by Formula 4 may be, but is not limited to, an example of the compound as represented by Formula 2 of the first aspect of the present disclosure.

In accordance with an illustrative embodiment, the aromatic aldehyde starting material includes, but is not limited to, a compound as represented by Formula 5, and the selenyl-substituted aromatic aldehyde compound includes, but is not limited to, a compound as represented by Formula 6:

[Formula 5]

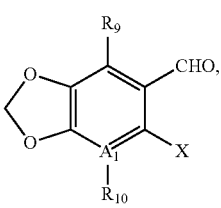

[Formula 6]

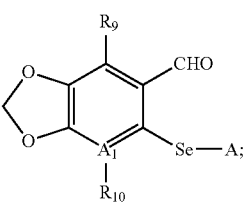

wherein each of the functional groups $R_9$ and $R_{10}$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including a halo group, a nitro group, a cyano group, and a carbonyl group; $A_1$ is C or N; and A and X are as defined in the first aspect of the present disclosure.

By way of example, the compound as represented by Formula 5 may be, but is not limited to, an example of the compound as represented by Formula 1 of the first aspect of the present disclosure, and the compound as represented by Formula 6 may be, but is not limited to, an example of the compound as represented by Formula 2 of the first aspect of the present disclosure.

In accordance with an illustrative embodiment, the aromatic aldehyde starting material includes, but is not limited to, a compound as represented by Formula 7, and the selenyl-substituted aromatic aldehyde compound includes, but is not limited to, a compound as represented by Formula 8:

[Formula 7]

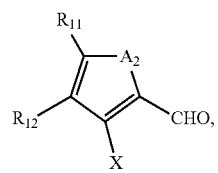

[Formula 8]

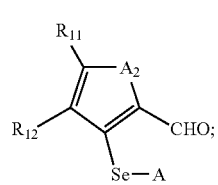

wherein each of the functional groups $R_{11}$ and $R_{12}$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including a halo group, a nitro group, a cyano group, and a carbonyl group; $A_2$ is O, S, or Se; and A and X are as defined in the first aspect of the present disclosure.

By way of example, the compound as represented by Formula 7 may be, but is not limited to, an example of the compound as represented by Formula 1 of the first aspect of the present disclosure, and the compound as represented by Formula 8 may be, but is not limited to, an example of the compound as represented by Formula 2 of the first aspect of the present disclosure.

In accordance with an illustrative embodiment of the present disclosure, the aromatic aldehyde starting material is added to the reaction mixture, and sequentially the base is added to the reaction mixture, but a sequence is not limited thereto.

By way of example, the aromatic aldehyde starting material may be added to the reaction mixture with stirring, and sequentially the base used for preparing the selenyl-substituted aromatic aldehyde compound may be added, but a sequence is not limited thereto. The stirring may be carried out for, but not limited to, about 10 minutes or more. When the base is added, the reducing agent containing the thiol group can be converted into negatively charged thiolate (RS⁻) and reducing power can be increased.

By way of example, a reaction of generating the negatively charged thiolate by using the reducing agent containing the thiol group can be displayed as shown in the following reaction mechanism:

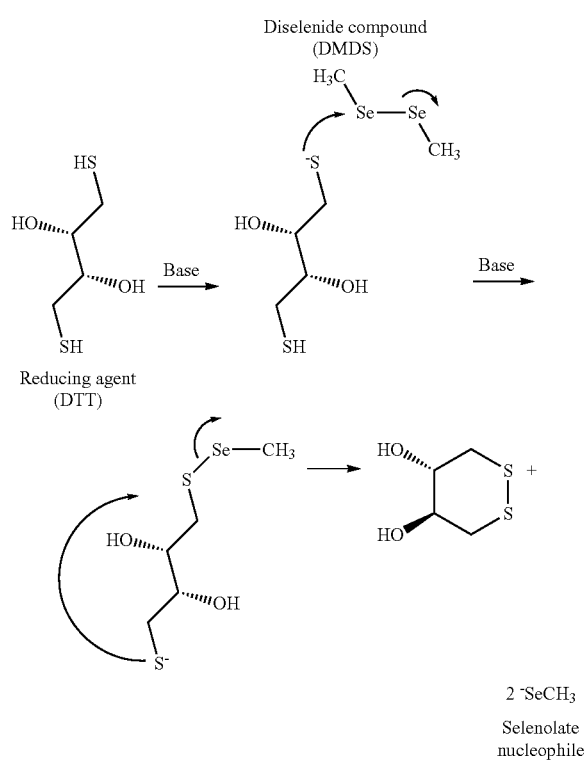

Meanwhile, there is a problem that the negatively charged thiolate is more highly reactive with the diselenide compound. That is, if the base is added at a first step which is preparing the reaction mixture in the above-described reaction, or if the base is added to the reaction mixture together with the aromatic aldehyde starting material, the negatively charged thiolate reacts with the diselenide compound rather than attacks an allyl group of the aromatic aldehyde starting material, so that a yield of a final product can be decreased. Therefore, after the aromatic aldehyde starting material is added and stirred for a certain period of time, the base is added during the reaction, so that the problem can be solved. Thus, the negatively charged thiolate attacks the allyl group of the aromatic aldehyde starting material to selectively perform a nucleophilic substitution reaction. As a result, the yield of the final product can be increased.

For this reason, an illustrative embodiment of the present disclosure provides a method for preparing a selenyl-substituted aromatic aldehyde compound, the method including, but not limited to, adding the aromatic aldehyde starting material to the reaction mixture with stirring and sequentially adding the base to the reaction mixture. By way of example, it was observed that when the aromatic aldehyde starting material was added to the reaction mixture containing the diselenide compound, a solvent, and a reducing agent and stirred for a certain period of time and then the base was added thereto, a nucleophilic substitution reaction was preferably performed within a few minutes at a position of a halo group contained in the aromatic aldehyde starting material, and a desired reaction product, selenyl-substituted aromatic aldehyde compound, was formed.

In accordance with an illustrative embodiment, the solvent includes a solvent selected from a group including, but not limited to, dimethylformaldehyde (DMF), dimethylsulfoxide (DMSO), tetrahydrofuran (THF), $CH_2Cl_2$, $CH_3CN$, $CH_3NO_2$, $CHCl_3$, $ClCH_2CH_2Cl$, alcohols, aromatic solvent, and combinations thereof.

By way of example, any solvent may be used without limit if it can easily dissolve the diselenide compound and the reducing agent contained in the reaction mixture.

By way of example, the alcohols which can be used as the solvent may include, but are not limited to, methanol, ethanol, propanol, or butanol, and the aromatic solvent may include, but is not limited to, benzene, toluene, or derivatives thereof.

In accordance with an illustrative embodiment, the reducing agent contains, but is not limited to, a thiol group.

By way of example, the reducing agent may include, but is not limited to, a material containing one or more thiol groups. By way of example, the reducing agent may include a material containing one or more thiol groups, for example, but not limited to, dithiothreitol (DTT), an isomer of dithiothreitol, cysteine, N-acetylcysteine, cysteine derivatives similar to N-boc-cysteine, or alkandithiol such as 1,4-butandithiol or 1,6-hexandithiol.

In order to prepare the selenyl-substituted aromatic aldehyde compound, in conventional methods, $NaBH_4$ or $LiEt_3BH$ that does not contain a thiol group has been used as a reducing agent. Further, metals such as indium, lanthanum, and samarium, and salts thereof have been used for reducing a Se—Se bond of the diselenide compound to form a selenolate nucleophile. However, it is difficult to obtain the selenyl-substituted aromatic aldehyde compound by the above-described conventional methods. That is because according to the conventional methods, a free aldehyde group of the aromatic aldehyde starting material may be reduced or converted into another functional group at the same time when the Se—Se bond of the diselenide compound is reduced.

Therefore, in accordance with the present disclosure, by using a material containing a thiol group as a reducing agent, it is possible to prevent a free aldehyde group of the aromatic aldehyde starting material from being reduced or converted into another functional group, and also possible to selectively reduce a Se—Se bond of the diselenide compound. As a result, as compared with conventional methods, it is possible to remarkably increase a yield of a desired reaction product. That is, by using a material containing a thiol group as a reducing agent, a yield of the selenyl-substituted aromatic aldehyde compound can be increased and unnecessary side reactions can be minimized, but the present disclosure is not limited thereto.

In accordance with an illustrative embodiment of the present disclosure, each of the functional groups $R_1$ to $R_4$ independently includes the electron withdrawing group selected from a group including a halo group, a nitro group, a cyano group, and a carbonyl group, and the base contains a weak base, but the present disclosure is not limited thereto.

In accordance with an illustrative embodiment of the present disclosure, the weak base includes, but is not limited to, $K_2CO_3$, $KHCO_3$, $Na_2CO_3$, $NaHCO_3$, NaOEt, $NH_4OH$, or combinations thereof.

In accordance with an illustrative embodiment of the present disclosure, each of the functional groups $R_1$ to $R_4$ independently includes the electron donating group selected from the group including an aromatic hydrocarbon group, an amine group, a $C_{1-10}$-alkyl group, a $C_{1-10}$-alkoxy group, and an ether group, and the base contains a strong base, but the present disclosure is not limited thereto.

In accordance with an illustrative embodiment of the present disclosure, the strong base includes, but is not limited to, DBU (1,8-diazabicyclo[5,4,0]undec-7-ene), KOH, NaOH, $Ca(OH)_2$, $Ba(OH)_2$, KOtBu, or combinations thereof.

In this regard, to increase a yield of a final product in accordance with the first aspect of the present disclosure, selenyl-substituted aromatic aldehyde compound as represented by Formula 2, if the aromatic aldehyde starting material as represented by Formula 1 contains an electron donating substituent, it is advantageous to use a strong base, whereas if the aromatic aldehyde starting material as represented by Formula 1 contains an electron withdrawing substituent, it is advantageous to use a weak base, but the present disclosure is not limited thereto.

That is, a kind of the base can be determined depending on a property of a substituent of the aromatic aldehyde starting material as represented by Formula 1, and the yield of the final product, selenyl-substituted aromatic aldehyde compound as represented by Formula 2, can be increased accordingly, but the present disclosure is not limited thereto.

By way of example, when a material containing an electron donating substituent is used as the aromatic aldehyde starting material as represented by Formula 1, if a weak base such as NaOEt is used, it is difficult to obtain the selenyl-substituted aromatic aldehyde compound, whereas if a strong base such as DBU is used, it is easy to obtain the selenyl-substituted aromatic aldehyde compound with a high yield, but the present disclosure is not limited thereto.

In accordance with an illustrative embodiment of the present disclosure, each of preparing the reaction mixture, and adding the aromatic aldehyde starting material and the base to the reaction mixture and reacting thereof is independently performed at from room temperature to about 100° C., but the present disclosure is not limited thereto.

By way of example, the reaction mixture may be prepared in a range of, but not limited to, from room temperature to about 100° C. The reaction mixture may be prepared in a range of, for example, but not limited to, from about 20° C. to about 40° C., from about 20° C. to about 60° C., from about 20° C. to about 80° C., from about 20° C. to about 100° C., from about 40° C. to about 60° C., from about 40° C. to about 80° C., from about 40° C. to about 100° C., from about 60° C. to about 80° C., from about 60° C. to about 100° C., or from about 80° C. to about 100° C.

Further, by way of example, the aromatic aldehyde starting material and the base may be added to the reaction mixture in a range of, but not limited to, from room temperature to about 100° C. The aromatic aldehyde starting material and the base may be added to the reaction mixture in a range of, for example, but not limited to, from about 20° C. to about 40° C., from about 20° C. to about 60° C., from about 20° C. to about 80° C., from about 20° C. to about 100° C., from about 40° C. to about 60° C., from about 40° C. to about 80° C., from about 40° C. to about 100° C., from about 60° C. to about 80° C., from about 60° C. to about 100° C., or from about 80° C. to about 100° C.

However, selection of a reaction temperature does not directly affect a high yield of the desired reaction product. Therefore, a reaction temperature can be selected without limit if it is not in a range which does not greatly affect reactivity. By way of example, the reaction mixture is prepared and stirred at room temperature, the aromatic aldehyde starting material is added to the reaction mixture and stirred at room temperature for a certain period of time, and the base is added thereto and stirred at room temperature, so that the selenyl-substituted aromatic aldehyde compound can be prepared, but the present disclosure is not limited thereto.

In accordance with an illustrative embodiment of the present disclosure, the reaction mixture includes the diselenide compound and the reducing agent of equivalence ratio of, but not limited to, from about 1:1/3 to about 1:3.

The reaction mixture may include the diselenide compound and the reducing agent of equivalence ratio of, for example, but not limited to, from about 1:1/3 to about 1:3, from about 1:1/3 to about 1:2, or from about 1:1/3 to about 1:1.

The equivalence ratio between the diselenide compound and the reducing agent can be adjusted without any specific limits if it is sufficient to reduce the Se—Se bond of the diselenide compound by the reducing agent and form a selenolate nucleophile required for the nucleophilic substitution reaction. Further, the equivalence ratio may vary depending on a kind of the diselenide compound and/or a kind of the reducing agent.

In accordance with an illustrative embodiment of the present disclosure, the diselenide compound as represented by general formula A-Se—Se-A is reduced by the reducing agent to form a selenolate nucleophile as represented by A-Se$^-$, and the selenolate nucleophile reacts with the aromatic aldehyde starting material to form the selenyl-substituted aromatic aldehyde compound by a nucleophilic substitution reaction, but the present disclosure is not limited thereto.

In the above-described illustrative embodiment, the reaction of reducing the diselenide compound by the reducing agent and forming the selenolate nucleophile can be displayed as shown in the following reaction mechanism. In the following reaction mechanism, by way of example, dimethyldiselenide (DMDS) is used as the diselenide compound and dithiothreitol (DTT) is used as the reducing agent, but the present disclosure is not limited thereto:

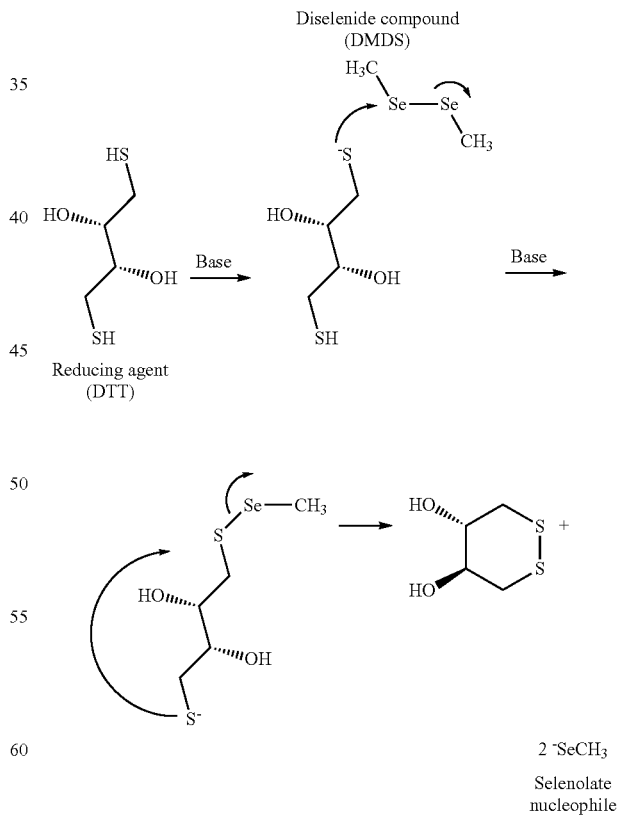

In accordance with a second aspect of the present disclosure, there is provided a selenyl-substituted aromatic aldehyde compound as represented by Formula 2:

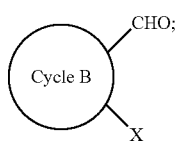

[Formula 2]

wherein A is a substitutable $C_{1-10}$-alkyl group, a substitutable $C_{1-10}$-alkoxycarbonyl-$C_{1-10}$-alkyl group, a substitutable allyl group, a substitutable aromatic cyclic group, a substitutable aromatic cyclic group substituted by one or two of a $C_{1-10}$-alkyl group, a substitutable aromatic cyclic group substituted by a halo group, or a substitutable aromatic cyclic group substituted by a nitro group; the cycle B includes one or more of functional groups $R_1$ to $R_4$; and the cycle B is a 5-membered heterocyclic ring or aromatic ring, a 6-membered heterocyclic ring or aromatic ring, or a heterocyclic ring or aromatic ring with the 5-membered ring fused to the 6-membered ring; and each of the 5-membered ring and the 6-membered ring includes 5 atoms and 6 atoms each selected from a group including C, N, O, S, and Se; and each of the functional groups $R_1$ to $R_4$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including a halo group, a nitro group, a cyano group, and a carbonyl group. X is a halo group.

In the second aspect, definitions and explanations of the A, the cycle B, and the functional groups $R_1$ to $R_4$ of Formula 2 are the same as described in the first aspect, and, thus, redundant explanations thereof will be omitted.

In accordance with an illustrative embodiment of the present disclosure, the selenyl-substituted aromatic aldehyde compound includes, but is not limited to, a compound as represented by Formula 4:

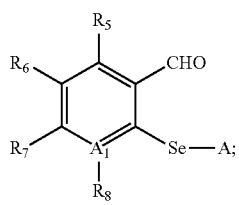

[Formula 4]

wherein each of the functional groups $R_5$ to $R_8$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including a halo group, a nitro group, a cyano group, and a carbonyl group; $A_1$ is C or N; and A is as defined in the second aspect of the present disclosure.

By way of example, the compound as represented by Formula 4 may be, but is not limited to, an example of the compound as represented by Formula 2 of the second aspect of the present disclosure.

In accordance with an illustrative embodiment of the present disclosure, the selenyl-substituted aromatic aldehyde compound includes, but is not limited to, a compound as represented by Formula 6:

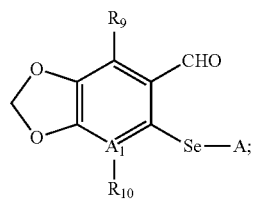

[Formula 6]

wherein each of the functional groups $R_9$ and $R_{10}$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including a halo group, a nitro group, a cyano group, and a carbonyl group; $A_1$ is C or N; and A is as defined in the second aspect of the present disclosure.

By way of example, the compound as represented by Formula 6 may be, but is not limited to, an example of the compound as represented by Formula 2 of the second aspect of the present disclosure.

In accordance with an illustrative embodiment of the present disclosure, the selenyl-substituted aromatic aldehyde compound includes, but is not limited to, a compound as represented by Formula 8:

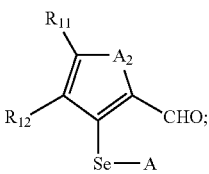

[Formula 8]

wherein each of the functional groups $R_{11}$ and $R_{12}$ is independently hydrogen; an electron donating group selected from a group including an aromatic hydrocarbon group, an amine group, a $C_{1-10}$-alkyl group, a $C_{1-10}$-alkoxy group, and an ether group; or an electron withdrawing group selected from a group including a halo group, a nitro group, a cyano group, and a carbonyl group; $A_2$ is O, S, or Se; and A is as defined in the second aspect of the present disclosure.

By way of example, the compound as represented by Formula 8 may be, but is not limited to, an example of the compound as represented by Formula 2 of the second aspect of the present disclosure.

Hereinafter, the present disclosure will be explained in more detail with reference to examples, but is not limited thereto.

EXAMPLES

All reagents used in the present Example are commercially available and used as being unprocessed unless specific description is provided to contrary.

<Synthesis Process>

Hereinafter, the selenyl-substituted aromatic aldehyde compound disclosed in the Example was prepared by the following synthesis process.

A diselenide compound as represented by general formula A-Se—Se-A, a solvent, and a reducing agent were prepared to prepare the reaction mixture. As the diselenide compound as represented by general formula A-Se—Se-A of the reaction mixture, a diselenide compound containing about 1.2 eq. of methyl group (Me), about 0.6 eq. of phenyl group (Ph), or about 0.6 eq. of benzyl group (Bn) as the A was used. As the solvent of the reaction mixture, anhydrous ethanol (EtOH) or dimethylformaldehyde (DMF) was used. As the reducing agent of the reaction mixture, about 1 eq. of dithiothreitol (DTT), about 1 eq. of N-acetylcysteine, or about 1 eq. of 1,4-butanedithiol was used.

To be more specific, the diselenide compound as represented by general formula A-Se—Se-A and the reducing agent were added to about 2 mL of the solvent. If the functional group A of the diselenide compound is a methyl group, an equivalence ratio between the diselenide compound and the reducing agent was about 1.2:1. Meanwhile, if the functional group A of the diselenide compound is a phenyl group or a benzyl group, the equivalence ratio between the diselenide compound and the reducing agent was about 0.6:1. The reaction mixture was stirred for about 30 minutes at room temperature or at about 80° C.

After the reaction mixture was prepared, an aromatic aldehyde compound as a starting material for preparing the selenyl-substituted aromatic aldehyde compound was added to the reaction mixture at a time. Then, the reaction mixture was stirred for about 15 minutes at room temperature or at about 80° C.

After the starting material was added to the reaction mixture and the reaction mixture was stirred, the base was added thereto. As the base, DBU as a strong base, $K_2CO_3$ or NaOEt as a weak base was used. About 2 eq. of the base was added to the reaction mixture at room temperature. Then, the reaction mixture was stirred for about 15 minutes at room temperature or at about 80° C.

After the base was added to the reaction mixture and the reaction mixture was stirred, it was checked by using thin layer chromatography (TLC) that the starting material was consumed completely. The solvent contained in the reaction mixture was removed in a vacuum and a crude solid was extracted three times by using about 25 mL of a solvent containing dichloromethane and water in a ratio of about 1:1. An organic phase collected by the extraction process was dried in an anhydrous environment by using $MgSO_4$, and the solvent was evaporated in a vacuum. The residue was refined by column chromatography using silica gel column. A pure product, i.e. the selenyl-substituted aromatic aldehyde compound as a target product in the present Example, was eluted by using ethyl acetate and hexane. A yield thereof is shown in the following Table 1 to Table 3.

The yield of the selenyl-substituted aromatic aldehyde compound varied depending on experimental conditions. To be specific, the yield was affected by what was used as the diselenide compound, the solvent, and the reducing agent contained in the reaction mixture, and what was used as the aromatic aldehyde starting material and the base added to the reaction mixture. An effect of a kind of the reducing agent on the yield was analyzed through the following Experimental Example 1, an effect of a kind of the base on the yield was analyzed through the following Experimental Example 2, and effects of a kind of the diselenide compound and a kind of the aromatic aldehyde starting material on the yield were analyzed through the following Experimental Example 3. Hereinafter, details thereof will be provided.

Experimental Example 1

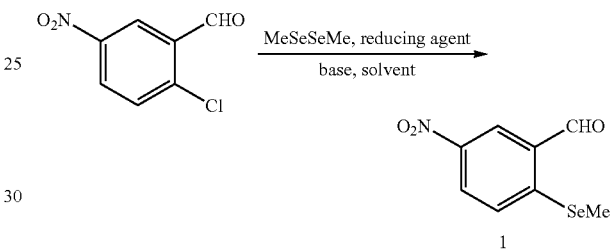

In Experimental Example 1, dimethyldiselenide (DMDS, MeSeSeMe) was used as the diselenide compound, and 5-nitro-2-chloro-benzaldehyde was used as the aromatic aldehyde starting material to prepare 2-methylselenyl-5-nitro-benzaldehyde as shown in the above reaction formula. The other materials, i.e. the solvent, the reducing agent, and the base, were not limited in kind and various kinds thereof were used for the experiment. Differences in % yield of the product caused by such differences in reaction conditions are shown in the following Table 1:

TABLE 1

| Entry | DMDS (eq.) | Reducing agent (eq.) | Base(eq.) | Solvent | Time (h) | Temp. (° C.) | Product (% yield) |
|---|---|---|---|---|---|---|---|
| 1 (Comparative Example) | 1 | NaBH$_4$ (1) | NaOEt | EtOH | 5 | 60 | 0 |
| 2 (Comparative Example) | 2 | NaBH$_4$ (2) | — | EtOH | 24 | Room temperature (RT) | 3 |
| 3 (Comparative Example) | 2 | NaBH$_4$ (2) | — | DMF | 24 | RT | 5 |
| 4 (Comparative Example) | 1 | NaBH$_4$ (1) | — | THF | 6 | 60 | 0 |
| 5 (Comparative Example) | 1 | — | K$_2$CO$_3$ (2.5) | DMF | 14 | 0 | — |
| 6 (Example) | 1 | DTT (1) | NaOEt (2) | EtOH | 4 | RT | 85 |
| 7 (Example) | 1 | DTT (2) | NaOEt (2) | DMF | 1 | RT | 85 |
| 8 (Example) | 1.2 | DTT (1) | K$_2$CO$_3$ (2.5) | DMF | 1 | RT | 85 |

TABLE 1-continued

| Entry | DMDS (eq.) | Reducing agent (eq.) | Base(eq.) | Solvent | Time (h) | Temp. (° C.) | Product (% yield) |
|---|---|---|---|---|---|---|---|
| 9 (Example) | 1.2 | DTT (1) | DBU (2) | DMF | 3 | RT | 84 |
| 10 (Example) | 1 | N-acetylcysteine (2) | NaOEt (2) | DMF | 1 | RT | 79 |
| 11 (Example) | 1.2 | N-acetylcysteine (2) | DBU (2) | DMF | 3 | RT | 79 |
| 12 (Example) | 1 | 1,4-butanedithiol (2) | NaOEt (2) | DMF | 2 | RT | 82 |
| 13 (Example) | 1.2 | 1,4-butanedithiol (2) | DBU (2) | DMF | 3 | RT | 82 |

As can be seen from Table 1, for Entry 1, NaBH₄ was used as the reducing agent for reducing a Se—Se bond of dimethyldiselenide (DMDS) as the diselenide compound. In this case, the Se—Se bond was not reduced to form a selenolate nucleophile and 2-methylselenyl-5-nitro-benzaldehyde as a desired product of a nucleophilic substitution reaction was not produced. Instead, a free aldehyde group of 5-nitro-2-chloro-benzaldehyde used as the starting material was reduced by the reducing agent and resultantly, alcohol was produced. Further, when NaBH₄ was used as the reducing agent at a high temperature, a Cannizzaro type reaction was preferably performed and the desired product was hardly obtained (see Entry 1 and Entry 4 of Table 1). It was observed through the experiment that as long as NaBH₄ was used as the reducing agent, even if other reaction conditions such as the solvent, the reaction time, the temperature, and an equivalent of the base were changed, the desired product was not obtained by performing a reaction as desired (see Entry 1 to Entry 4 of Table 1).

Meanwhile, for Entry 6 to Entry 13, the reducing agent was changed and resultantly, a sufficient yield was obtained. To be specific, for Entry 6 to Entry 9, dithiothreitol (DTT) was used as the reducing agent, and a side reaction in which the free aldehyde of the aromatic aldehyde starting material was reduced or converted into another functional group by the reducing agent was not performed. Therefore, the yield of the desired reaction product was remarkably increased. As long as dithiothreitol (DTT) was used as the reducing agent, even if other reaction conditions such as the base or the solvent were changed, the yield of the product was kept high. Further, even if the reducing agent was changed to a different material containing a thiol group such as N-acetylcysteine or 1,4-butanedithiol, the desired product was obtained with a high yield (see Entry 10 to Entry 13 of Table 1).

From the experimental result of Experimental example 1 as shown in Table 1, it was found that if a material containing a thiol group such as dithiothreitol, N-acetylcysteine, or 1,4-butanedithiol was used as the reducing agent, the side reaction in which the free aldehyde of the aromatic aldehyde starting material was reduced or converted into another functional group was not performed, and, thus, the selenyl-substituted aromatic aldehyde compound as the desired product was obtained with a high yield.

Experimental Example 2

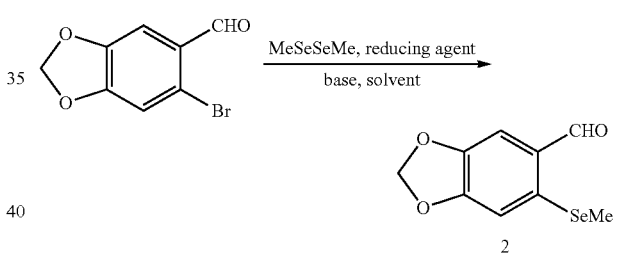

In Experimental Example 2, dimethyldiselenide (DMDS, MeSeSeMe) was used as the diselenide compound, and 4,5-methylenedioxy-2-bromo-benzaldehyde was used as the aromatic aldehyde starting material to prepare 4,5-methylenedioxy-2-methylselanyl-benzaldehyde as shown in the above reaction formula. The other materials, i.e. the solvent, the reducing agent, and the base, were not limited in kind and various kinds thereof were used for the experiment. Differences in % yield of the product caused by such differences in reaction conditions are shown in the following Table 2:

TABLE 2

| Entry (Example) | Reducing agent(eq.) | Base (eq.) | Solvent | DMDS (eq.) | Time (h) | Temperature (° C.) | Product (% yield) |
|---|---|---|---|---|---|---|---|
| 1 | DTT (1) | NaOEt (2) | EtOH | 1 | 24 | RT | — |
| 2 | DTT (1) | NaOEt (2) | DMF | 1 | 24 | RT | — |
| 3 | DTT (1) | NaOEt (2) | DMF | 1 | 24 | 60 | — |
| 4 | DTT (1) | DBU (2) | DMF | 1 | 1 | RT | 80 |
| 5 | DTT (1) | DBU (2.5) | DMF | 1.2 | 1 | RT | 82 |

TABLE 2-continued

| Entry (Example) | Reducing agent(eq.) | Base (eq.) | Solvent | DMDS (eq.) | Time (h) | Temperature (° C.) | Product (% yield) |
|---|---|---|---|---|---|---|---|
| 6 | N-acetylcysteine (2) | DBU (2.5) | DMF | 1.5 | 3 | RT | 56 |
| 7 | 1,4-butanedithiol (2) | DBU (2.5) | DMF | 1.5 | 3 | RT | 60 |

As can be seen from Table 2, for Entry 1 to Entry 3, dithiothreitol (DTT) was used as the reducing agent for reducing the Se—Se bond of dimethyldiselenide (DMDS) as the diselenide compound. According to Experimental Example 1, when the reducing agent containing a thiol group was used, the desired product was obtained with a high yield. However, although dithiothreitol containing two thiol groups were used as the reducing agent for Entry 1 to Entry 3, the desired product was not obtained. To be specific, as for Entry 1 and Entry 2, the experiment was carried out at room temperature and a byproduct was produced. As for Entry 3, the experiment was carried out at a high temperature of about 60° C. and an ethoxide substitution reaction was performed by NaOEt as the base, so that an ethyl ether analogue was produced. From the experimental results of Entry 1 to Entry 3, it was found that when the reducing agent containing a thiol group was used, if an appropriate base was not used, the desired product was not obtained.

Meanwhile, from the experimental results of Entry 4 to Entry 7, it was found that when an appropriate base was used, even if other reaction conditions for Entry 1 to Entry 3 were not changed, the desired product was obtained with a high yield. To be specific, if an aldehyde starting material was an aromatic aldehyde starting material having an electron donating substituent such as 4,5-methylenedioxy-2-bromo-benzaldehyde, the desired product was obtained with a high yield only when a strong base such as DBU was used (see Entry 4 to Entry 7 of Table 2), and when a weak base such as NaOEt was used, the desired product was not obtained (see Entry 1 to Entry 3 of Table 2).

From the experimental result of Experimental example 2 as shown in Table 2, it was found that even if a material containing a thiol group such as dithiothreitol, N-acetylcysteine, or 1,4-butanedithiol was used as the reducing agent, the desired product was not necessarily obtained with a high yield, and selection of the base was also an important reaction condition. To be specific, if the aromatic aldehyde starting material having an electron donating substituent was used as the starting material, the desired product, selenyl-substituted aromatic aldehyde compound, was obtained with a high yield only when a strong base was used.

Although not shown in Table 2, it was found through Experimental Example 2 that a process of adding a base greatly affected reactivity in the reaction for preparing the selenyl-substituted aromatic aldehyde compound. To be specific, it was observed that when the base was added to the reaction mixture containing the diselenide compound, the solvent, and the reducing agent, and the aldehyde starting material, the nucleophilic substitution reaction was preferably performed within a few minutes at a position of a halo group contained in the aromatic aldehyde starting material, and the desired reaction product was formed. Further, it was observed that after the base was added, the yield of the product was decreased gradually as time went by. From the results obtained through Experimental Example 2, it was found that the selection of a base and the process of adding the base greatly affected the reactivity in the reaction preparing the selenyl-substituted aromatic aldehyde compound.

Experimental Example 3

In Experimental Example 3, dithiothreitol (DTT) was used as the reducing agent and dimethylformaldehyde (DMF) was used as the solvent to prepare a selenyl-substituted aromatic aldehyde compound. The diselenide compound as represented by general formula A-Se—Se-A, the aromatic aldehyde starting material, and the base were not limited in kind and various kinds thereof were used for the experiment.

To be specific, as the diselenide compound, dimethyldiselenide having a methyl group (Me) as the functional group A, diphenyldiselenide having a phenyl group (Ph) as the functional group A, or dibenzyldiselenide having a benzyl group (Bn) as the functional group A was used. As the aromatic aldehyde starting material, various aromatic aldehyde materials having an electron donating substituent or an electron withdrawing substituent were used. Formulas thereof are provided in the following Table 3. Further, as the base, $K_2CO_3$ as a weak base or DBU as a strong base was used. In all cases, about 2.5 eq. of the base was used. Differences in % yield of the product caused by such differences in reaction conditions are shown in the following Table 3.

In the following Table 3, $K_2CO_3$ was used as the base and a reaction temperature was kept at about 80° C. for reaction condition A, $K_2CO_3$ was used as the base and a reaction temperature was kept at room temperature for reaction condition A', DBU was used as the base and a reaction temperature was kept at room temperature for reaction condition B, and DBU was used as the base and a reaction temperature was kept at about 80° C. for reaction condition C:

TABLE 3

| Entry (Example) | Aldehyde starting material | Functional group A of diselenide (eq.) | Reaction condition | Yield (%) |
|---|---|---|---|---|
| 1 | ⌬-CHO, Br | Me (1.2) | B | 84 |
| 2 | ⌬-CHO, Br | Ph (0.6) | C | 80 |
| 3 | ⌬-CHO, Br | Bn (0.6) | C | 58 |

TABLE 3-continued

| Entry (Example) | Aldehyde starting material | Functional group A of diselenide (eq.) | Reaction condition | Yield (%) |
|---|---|---|---|---|
| 4 | 2-F-C6H4-CHO | Me (1.2) | B | 97 |
| 5 | 2-Br-3-NO2-C6H3-CHO | Me (1.2) | A' | 79 |
| 6 | 4-Cl-3-NO2... | Me (1.2) | A' | 85 |
| 7 | (O2N, Cl)-C6H3-CHO | Ph (0.6) | A | 97 |
| 8 | (O2N, Cl)-C6H3-CHO | Bn (0.6) | A | 69 |
| 9 | (O2N, Cl)-C6H3-CHO | 4-Cl—Bn (0.6) | A | 68 |
| 10 | (O2N, Cl)-C6H3-CHO | 4-NO2—Bn (0.6) | A | 60 |
| 11 | (O2N, Cl)-C6H3-CHO | 3-Me—Bn (0.6) | A | 96 |
| 12 | (O2N, Cl)-C6H3-CHO | 3,5-diMe—Bn (0.6) | A | 96 |
| 13 | (F3C, Cl)-C6H3-CHO | Me (1.2) | A' | 75 |
| 14 | (F3C, Cl)-C6H3-CHO | Ph (0.6) | A' | 74 |
| 15 | (F3C, Cl)-C6H3-CHO | Bn (0.6) | A' | 73 |
| 16 | (F3C, Cl)-C6H3-CHO | 4-Cl—Bn (0.6) | A' | 68 |
| 17 | (F3C, Cl)-C6H3-CHO | 3-Me—Bn (0.6) | A' | 70 |
| 18 | (F3C, Cl)-C6H3-CHO | 3,5-diMe—Bn (0.6) | A' | 71 |
| 19 | (H3C, F)-C6H3-CHO | Me (1.2) | B | 85 |
| 20 | (Cl, OCH3)-C6H3-CHO | Me (1.2) | B | 60 |
| 21 | (H3CO, F)-C6H3-CHO | Me (1.2) | B | 92 |
| 22 | (MeO, Br)-C6H3-CHO | Me (1.2) | B | 60 |
| 23 | (MeO, Br)-C6H3-CHO | Ph (0.6) | C | 62 |
| 24 | (MeO, Br)-C6H3-CHO | Bn (0.6) | C | 39 |
| 25 | methylenedioxy-Br-C6H2-CHO | Me (1.2) | B | 82 |
| 26 | methylenedioxy-Br-C6H2-CHO | Ph (0.6) | C | 60 |
| 27 | methylenedioxy-Br-C6H2-CHO | Bn (0.6) | C | 40 |

TABLE 3-continued

| Entry (Example) | Aldehyde starting material | Functional group A of diselenide (eq.) | Reaction condition | Yield (%) |
|---|---|---|---|---|
| 28 | H₃CO-/H₃CO- substituted benzaldehyde with F (CHO) | Me (1.2) | B | 67 |
| 29 | Cl, NO₂ substituted benzaldehyde (CHO) | Me (1.2) | A' | 67 |
| 30 | 2-Cl pyridine-3-carbaldehyde (CHO) | Me (1.2) | A' | 70 |
| 31 | 2-Cl pyridine-3-carbaldehyde (CHO) | Ph (0.6) | A' | 62 |
| 32 | 3-Bromo-furan-2-carbaldehyde | Me (1.2) | A' | 78 |
| 33 | 3-Bromo-thiophene-2-carbaldehyde | Me (1.2) | A' | 92 |

<Analysis data of ¹H NMR and ¹³C NMR of selenyl-substituted aromatic aldehyde compound produced in Entry 1 to Entry 33 shown in Table 3>

[Entry 1] 2-Methylselanyl-benzaldehyde

¹H NMR (500.1 MHz, CDCl₃) ∂ 2.27 (s, 3H), 7.32 (td, 1H, J=8.0, 1.0), 7.43 (d, 1H, J=8.0), 7.47 (td, 1H, J=8.5, 1.5), 7.77 (dd, 1H, J=8.0, 1.5), 10.12 (s, 1H); ¹³C NMR (125.7 MHz, CDCl₃) ∂ 5.43, 124.45, 127.48, 133.42, 133.85, 135.08, 138.26, 192.04.

[Entry 2] 2-Phenylselanyl-benzaldehyde

¹H NMR (500.1 MHz, CDCl₃) ∂ 7.03 (d, 1H, J=8.0), 7.30-7.32 (m, 2H), 7.41-7.44 (m, 3H), 7.65 (dd, 2H, J=8.0, 1.5), 7.83 (dd, 1H, J=7.0, 2.0), 10.19 (s, 1H); ¹³C NMR (125.7 MHz, CDCl₃) ∂ 125.49, 128.18, 129.07, 129.81, 130.02, 133.76, 133.81, 134.94, 136.73, 139.55, 192.54.

[Entry 3] 2-Benzylselanyl-benzaldehyde

¹H NMR (500.1 MHz, CDCl₃) ∂ 4.12 (s, 2H), 7.21-7.29 (m, 5H), 7.36 (dd, 1H, J=7.5, 1.0), 7.46 (dd, 1H, J=6.0, 1.5), 7.57 (d, 1H, J=8.0), 7.80 (dd, 1H, J=7.5, 1.5), 10.11 (s, 1H); ¹³C NMR (125.7 MHz, CDCl₃) ∂ 30.70, 126.09, 127.18, 128.66, 129.12, 130.94, 133.84, 133.93, 135.06, 136.89, 137.86, 192.73.

[Entry 4] 2-Methylselanyl-benzaldehyde

¹H NMR (500.1 MHz, CDCl₃) ∂ 2.27 (s, 3H), 7.32 (td, 1H, J=8.0, 1.0), 7.43 (d, 1H, J=8.0), 7.47 (td, 1H, J=8.5, 1.5), 7.77 (dd, 1H, J=8.0, 1.5), 10.12 (s, 1H); ¹³H NMR (125.7 MHz, CDCl₃) ∂ 5.43, 124.45, 127.48, 133.42, 133.85, 135.08, 138.26, 192.04.

[Entry 5] 2-Methylselanyl-6-nitro-benzaldehyde

¹H NMR (500.1 MHz, CDCl₃) ∂ 2.26 (s, 3H), 7.27 (d, 1H, J=1.0), 7.34-7.39 (m, 2H), 10.66 (s, 1H); ¹³C NMR (125.7 MHz, CDCl₃) ∂ 4.57, 124.29, 124.65, 127.98, 131.91, 139.26, 141.08, 189.01.

[Entry 6] 2-methylselenyl-5-nitro-benzaldehyde

¹H NMR (500.1 MHz, CDCl₃) ∂ 2.40 (s, 1H), 7.61 (d, 1H, J=9.0), 8.29 (dd, 1H, J=8.5, 2.5), 8.64 (d, 1H, J=2.5), 10.18 (s, 1H); ¹³C NMR (125.7 MHz, CDCl₃) ∂ 6.54, 126.99, 128.13, 129.91, 133.90, 145.06, 149.42, 190.44.

[Entry 7] 5-Nitro-2-phenylselanyl-benzaldehyde

¹H NMR (500.1 MHz, CDCl₃) ∂ 7.10 (d, 1H, J=8.5), 7.47-7.56 (m, 3H), 7.68 (dd, 2H, J=8.5, 2.0), 8.05 (dd, 1H, J=8.5, 2.5), 8.66 (d, 1H, J=2.5), 10.22 (s, 1H); ¹³C NMR (125.7 MHz, CDCl₃) ∂ 126.13, 126.47, 129.23, 129.56, 129.73, 129.92, 132.68, 136.69, 144.94, 150.06, 190.08.

[Entry 8] 2-Benzylselanyl-5-nitro-benzaldehyde

¹H NMR (500.1 MHz, CDCl₃) ∂ 4.19 (s, 2H), 7.12-7.22 (m, 5H), 7.99-8.04 (m, 2H), 8.58 (d, 1H, J=2.0), 10.12 (s, 1H); ¹³C NMR (125.7 MHz, CDCl₃) ∂ 29.65, 126.09, 126.67, 127.92, 128.17, 128.43, 128.47, 133.16, 134.23, 144.36, 148.10, 189.47.

[Entry 9] 2-(4-Chloro-benzylselanyl)-5-nitro-benzaldehyde

¹H NMR (500.1 MHz, CDCl₃) ∂ 4.22 (s, 2H), 7.29-7.34 (m, 4H), 7.68 (d, 1H, J=9.0), 8.27 (dd, 1H, J=8.5, 2.5), 8.65 (d, 1H, J=2.5), 10.16 (s, 1H); ¹³H NMR (125.7 MHz, CDCl₃) ∂ 27.48, 124.94, 126.88, 127.00, 127.35, 128.25, 131.33, 131.61, 131.90, 143.21, 146.41, 188.23.

[Entry 10] 5-Nitro-2-(4-nitro-benzylselanyl)-benzaldehyde

¹H NMR (500.1 MHz, CDCl₃) ∂ 4.32 (s, 2H), 7.57 (d, 2H, J=9.0), 7.66 (d, 1H, J=9.0), 8.21 (d, 2H, J=8.5), 8.31 (dd, 1H, J=9.0, 2.5), 8.68 (d, 1H, J=2.5), 10.17 (s, 1H); ¹³C NMR (125.7 MHz, CDCl₃) ∂ 29.48, 124.22, 127.40, 129.01, 129.88, 130.09, 134.18, 143.35, 145.69, 147.44, 147.76, 190.93.

[Entry 11] 2-(3-Methyl-benzylselanyl)-5-nitro-benzaldehyde

¹H NMR (500.1 MHz, CDCl₃) ∂ 2.34 (s, 3H), 4.22 (s, 2H), 7.09 (d, 1H, J=7.0), 7.17-7.23 (m, 3H), 7.72 (d, 1H, J=9.0), 8.27 (dd, 1H, J=9.0, 2.5), 8.64 (d, 1H, J=2.5), 10.15 (s, 1H); ¹³C NMR (125.7 MHz, CDCl₃) ∂ 19.68, 29.01, 124.51, 125.36, 126.69, 127.17, 127.69, 127.77, 128.16, 132.43, 133.38, 137.04, 143.68, 147.62, 188.72.

[Entry 12] 2-(3,5-Dimethyl-benzylselanyl)-5-nitro-benzaldehyde $^1$H NMR (500.1 MHz, CDCl$_3$) ∂ 2.29 (s, 6H), 4.18 (s, 2H), 6.91 (s, 1H), 6.99 (s, 2H), 7.72 (d, 1H, J=8.5), 8.26 (dd, 1H, J=8.5, 2.5), 8.63 (d, 1H, J=2.5), 10.15 (s, 1H); $^{13}$C NMR (125.7 MHz, CDCl$_3$) ∂ 21.14, 30.63, 126.90, 127.00, 129.32, 129.35, 129.39, 134.07, 134.86, 138.50, 145.25, 149.44, 190.38.

[Entry 13] 2-Methylselanyl-5-trifluoromethyl-benzaldehyde $^1$H NMR (500.1 MHz, CDCl$_3$) ∂ 2.34 (s, 3H), 7.56 (d, 1H, J=8.5), 7.68 (dd, 1H, J=8.5, 1.0), 8.02 (s, 1H), 10.16 (s, 1H); $^{13}$C NMR (125.7 MHz, CDCl$_3$) ∂ 5.72, 124.44, 126.57, 126.61, 126.83, 127.10, 127.36, 127.77, 129.16, 129.19, 131.51, 131.54, 133.65, 143.99, 190.74.

[Entry 14] 2-Phenylselanyl-5-trifluoromethyl-benzaldehyde $^1$H NMR (500.1 MHz, CDCl$_3$) ∂ 7.09 (d, 1H, J=8.5), 7.44-7.52 (m, 4H), 7.67-7.68 (m, 2H), 7.68 (s, 1H), 8.05 (s, 1H), 10.20 (s, 1H); $^{13}$C NMR (125.7 MHz, CDCl$_3$) ∂ 120.64, 125.22, 125.80, 126.07, 127.64, 127.67, 127.70, 127.87, 128.11, 128.26, 129.75, 129.77, 131.43, 135.24, 143.65, 189.30.

[Entry 15] 2-Benzylselanyl-5-trifluoromethyl-benzaldehyde $^1$H NMR (500.1 MHz, CDCl$_3$) ∂ 4.21 (s, 2H), 7.27-7.37 (m, 5H), 7.67-7.71 (m, 2H), 8.05 (s, 1H), 10.13 (s, 1H); $^{13}$C NMR (125.7 MHz, CDCl$_3$) ∂ 29.30, 126.18, 127.52, 127.84, 128.37, 128.39, 129.02, 129.64, 133.29, 134.68, 189.92.

[Entry 16] 2-(4-Chloro-phenylselanyl)-5-trifluoromethyl-benzaldehyde $^1$H NMR (500.1 MHz, CDCl$_3$) ∂ 4.16 (s, 2H), 7.26 (s, 1H), 7.27 (s, 3H), 7.63-7.70 (m, 2H), 8.05 (s, 1H), 10.15 (s, 1H); $^{13}$C NMR (125.7 MHz, CDCl$_3$) ∂ 27.76, 120.67, 122.84, 126.23, 126.50, 127.17, 127.88, 127.91, 127.94, 127.96, 128.07, 128.64, 129.40, 129.42, 129.45, 131.50, 132.62, 132.77, 141.59, 189.38.

[Entry 17] 2-(3-Methyl-benzylselanyl)-5-trifluoromethyl-benzaldehyde $^1$H NMR (500.1 MHz, CDCl$_3$) ∂ 2.23 (s, 3H), 4.06 (s, 2H), 6.97 (d, 1H, J=7.5), 7.04 (s, 1H), 7.05 (s, 1H), 7.10-7.17 (m, 1H), 7.57-7.61 (m, 2H), 7.94 (s, 1H), 10.04 (s, 1H); $^{13}$C NMR (125.7 MHz, CDCl$_3$) ∂ 21.30, 30.90, 124.69, 126.15, 128.26, 128.70, 129.64, 129.67, 129.86, 130.42, 130.86, 134.63, 135.80, 138.54, 191.60, 207.05.

[Entry 18] 2-(3,5-Dimethyl-benzylylselanyl)-5-trifluoromethyl-benzaldehyde $^1$H NMR (500.1 MHz, CDCl$_3$) ∂ 2.28 (s, 6H), 4.12 (s, 2H), 6.89 (s, 1H), 6.94 (s, 2H), 7.66-7.71 (m, 2H), 8.04 (s, 1H), 10.13 (s, 1H); $^{13}$C NMR (125.7 MHz, CDCl$_3$) ∂ 20.13, 29.61, 121.55, 123.66, 127.00, 128.12, 128.57, 128.59, 129.39, 129.73, 129.76, 133.57, 134.54, 137.36, 190.18.

[Entry 19] 5-Methyl-2-methylselanyl-benzaldehyde $^1$H NMR (500.1 MHz, CDCl$_3$) ∂ 2.27 (s, 3H), 2.39 (s, 3H), 7.31 (d, 1H, J=8), 7.35 (d, 1H, J=8), 7.61 (s, 1H), 10.13 (s, 1H); $^{13}$H NMR (125.7 MHz, CDCl$_3$) ∂ 5.20, 19.72, 127.56, 133.55, 133.93, 134.14, 134.18, 134.76, 191.85.

[Entry 20] 3-Methoxy-2-methylselanyl-benzaldehyde $^1$H NMR (500.1 MHz, CDCl$_3$) ∂ 2.29 (s, 3H), 3.96 (s, 3H), 7.09 (d, 1H, J=8.0), 7.41 (t, 1H, J=8.0), 7.53 (d, 1H, J=7.5), 10.67 (s, 1H); $^{13}$H NMR (125.7 MHz, CDCl$_3$) ∂ 9.40, 56.34, 115.56, 120.92, 124.27, 129.44, 138.67, 160.21, 194.05.

[Entry 21] 4-Methoxy-2-methylselanyl-benzaldehyde $^1$H NMR (500.1 MHz, CDCl$_3$) ∂ 2.22 (s, 3H), 3.86 (s, 3H), 6.78 (dd, 1H, J=8.5, 2.5), 6.87 (d, 1H, J=2.0), 7.67 (d, 1H, J=8.5), 9.93 (s, 1H); $^{13}$C NMR (125.7 MHz, CDCl$_3$) ∂ 3.53, 53.44, 107.55, 111.57, 125.89, 135.57, 138.76, 161.64, 188.50.

[Entry 22] 5-Methoxy-2-methylselanyl-benzaldehyde $^1$H NMR (500.1 MHz, CDCl$_3$) ∂ 2.29 (s, 3H), 3.86 (s, 3H), 7.10 (dd, 1H, J=8.5, 3.0), 7.37 (d, 1H, J=3.0), 7.44 (d, 1H, J=9.0), 10.26 (s, 1H); $^{13}$C NMR (125.7 MHz, CDCl$_3$) ∂ 5.05, 53.36, 114.60, 119.16, 125.76, 129.41, 133.35, 156.02, 190.28.

[Entry 23] 5-Methoxy-2-phenylselanyl-benzaldehyde $^1$H NMR (500.1 MHz, CDCl$_3$) ∂ 3.87 (s, 3H), 7.01 (dd, 1H, J=9.0, 3.0), 7.28 (s, 1H), 7.33-7.34 (m, 3H), 7.44 (d, J=3.0), 7.48-7.50 (m, 2H), 10.33 (s, 1H); $^{13}$H NMR (125.7 MHz, CDCl$_3$) ∂ 55.53, 115.75, 121.66, 127.38, 128.00, 129.66, 130.40, 133.97, 134.89, 136.06, 159.09, 192.83.

[Entry 24] 2-Benzylselanyl-5-methoxy-benzaldehyde $^1$H NMR (500.1 MHz, CDCl$_3$) ∂ 3.85 (s, 3H), 4.00 (s, 2H), 7.04-7.08 (m, 3H), 7.18-7.22 (m, 3H), 7.36 (d, 1H, J=3.0), 7.53 (d, 1H, J=9.0), 10.09 (s, 1H); $^{13}$H NMR (125.7 MHz, CDCl$_3$) ∂ 31.83, 54.30, 112.10, 120.36, 124.40, 125.81, 127.24, 127.56, 136.17, 136.41, 136.67, 158.46, 191.97.

[Entry 25] 6-Methylselanyl-benzo[1,3]dioxole-5-carbaldehyde $^1$H NMR (500.1 MHz, CDCl$_3$) 2.16 (s, 3H), 5.96 (s, 2H), 6.82 (s, 1H), 7.13 (s, 1H), a 9.92 (s, 1H); $^{13}$C NMR (125.7 MHz, CDCl$_3$) ∂ 6.66, 101.60, 108.77, 111.34, 128.29, 133.30, 145.82, 152.20, 189.58.

[Entry 26] 6-Phenylselanyl-benzo[1,3]dioxole-5-carbaldehyde $^1$H NMR (500.1 MHz, CDCl$_3$) ∂ 6.01 (s, 2H), 6.64 (s, 1H), 7.31 (s, 1H), 7.36-7.39 (m, 3H), 7.56-7.58 (m, 2H), 10.11 (s, 1H); $^{13}$C NMR (125.7 MHz, CDCl$_3$) ∂ 100.98, 110.26, 110.48, 127.49, 127.70, 128.15, 128.56, 132.84, 134.09, 145.90, 151.60, 189.35.

[Entry 27] 6-(Benzylselanyl)-benzo[1,3]dioxole-5-carbaldehyde $^1$H NMR (500.1 MHz, CDCl$_3$) ∂ 4.04 (s, 2H), 6.07 (s, 2H), 7.15 (s, 1H), 7.16 (s, 1H), 7.21-7.25 (m, 3H), 7.30 (s, 1H), 9.99 (s, 1H); $^{13}$C NMR (125.7 MHz, CDCl$_3$) ∂ 31.66, 101.00, 108.43, 112.80, 125.98, 127.35, 127.67, 130.03, 130.13, 135.95, 146.69, 151.30, 190.01.

[Entry 28]
4,5-Dimethoxy-2-methylselanyl-benzaldehyde $^1$H NMR (500.1 MHz, CDCl$_3$) ∂ 2.32 (s, 3H), 3.94 (s, 3H), 3.99 (s, 3H), 7.00 (s, 1H), 7.36 (s, 1H) 10.20 (s, 1H); $^{13}$C NMR (125.7 MHz, CDCl$_3$) ∂ 7.80, 56.15, 56.18, 113.16, 113.91, 128.32, 131.02, 147.87, 153.82, 191.14.

[Entry 29] 4-Methylselanyl-3-nitro-benzaldehyde $^1$H NMR (500.1 MHz, CDCl$_3$) ∂ 2.40 (s, 3H), 7.67 (d, 1H, J=8.5), 8.03 (dd, 1H, J=8.5, 2), 8.77 (d, 1H, J=1.5), 10.04 (s, 1H); $^{13}$C NMR (125.7 MHz, CDCl$_3$) ∂ 8.10, 128.15, 129.27, 131.83, 133.62, 143.47, 146.57, 189.28.

[Entry 30] 2-Methylselanyl-pyridine-3-carbaldehyde $^1$H NMR (500.1 MHz, CDCl$_3$) ∂ 2.42 (s, 3H), 7.20 (dd, 1H, J=7.5, 4.5), 7.95 (dd, 1H, J=7.5, 1.5), 8.60 (dd, 1H, J=4.5, 1.5), 10.10 (s, 1H); $^{13}$C NMR (125.7 MHz, CDCl$_3$) ∂ 3.61, 117.42, 128.67, 139.74, 151.54, 158.87, 189.35.

[Entry 31] 2-Phenylselanyl-pyridine-3-carbaldehyde $^1$H NMR (500.1 MHz, CDCl$_3$) ∂ 7.22 (dd, 1H, J=7.5, 4.5), 7.39-7.42 (m, 3H), 7.65-7.66 (m, 2H), 8.02 (dd, 1H, J=7.5, 1.5), 8.47 (dd, 1H, J=5.0, 2.0), 10.20 (s, 1H); $^{13}$C NMR (125.7 MHz, CDCl$_3$) ∂ 118.04, 125.68, 126.62, 127.03, 127.91, 134.41, 139.09, 151.60, 158.99, 189.16.

[Entry 32] 3-Methylselanyl-furan-2-carbaldehyde $^1$H NMR (500.1 MHz, CDCl$_3$) ∂ 2.32 (s, 3H), 6.57 (d, 1H, J=1.5), 7.60 (d, 1H, J=2.0), 9.76 (s, 1H); $^{13}$C NMR (125.7 MHz, CDCl$_3$) ∂ 5.68, 113.32, 126.00, 147.16, 148.39, 177.40.

[Entry 33]
3-Methylselanyl-thiophene-2-carbaldehyde $^1$H NMR (500.1 MHz, CDCl$_3$) ∂ 2.41 (s, 3H), 7.13 (d, 1H, J=5.0), 7.72 (d, 1H, J=5.0), 9.98 (s, 1H); $^{13}$C NMR (125.7 MHz, CDCl$_3$) ∂ 7.65, 130.13, 134.50, 136.28, 138.39, 182.25

According to Table 3 showing the experimental results of Experimental Example 3, when dimethyldiselenide or diphenyldiselenide was used as the diselenide compound, the reaction was carried out smoothly and the desired product was obtained with a high yield. However, when dibenzyldiselenide was used as the diselenide compound, the yield of the reaction product varied depending on a kind of the aromatic aldehyde starting material.

To be specific, when dibenzyldiselenide was used as the diselenide compound, and a material having an electron donating group such as an aromatic hydrocarbon group, an amine group, or an ether group was used as the aromatic aldehyde starting material, it was difficult to nucleophilically substitute a halo group of the aromatic aldehyde starting material with benzylselenolate as a nucleophile. Therefore, it was observed that the yield of the desired product was low (see Entry 24 and Entry 27 of Table 3). This result was similar for a case where 3-methyl-dibenzyldiselenide (3-Me-Bn of Table 3), 3,5-dimethyl-dibenzyldiselenide (3,5-diMe-Bn of Table 3), 4-nitro-dibenzyldiselenide (4-NO$_2$-Bn of Table 3), or 4-chloro-dibenzyldiselenide (4-Cl-Bn of Table 3) obtained by substituting some functional groups of dibenzyldiselenide was used as the diselenide compound.

In these cases, it was observed that the yield of the product was low. That was because benzylselenolate as a selenolate nucleophile formed by reducing a Se—Se bond of dibenzyldiselenide used as the diselenide compound was not as strong as other selenolate nucleophiles. Further, that was because an electron density of the aromatic aldehyde starting material having an electron donating group was much higher at a position of the halo group where a nucleophilic substitution reaction was performed by the selenolate nucleophile than at a position of the free aldehyde group. For these reasons, when dibenzyldiselenide was used as the diselenide compound, and the material having the electron donating group was used as the aromatic aldehyde starting material, the reaction was carried out along a different path. Therefore, the yield of the desired product, selenyl-substituted aromatic aldehyde compound, was low and a byproduct and a Cannizzaro type reaction product were produced.

From the experimental results of Experimental Example 3 as shown in Table 3, it was found that selection of the aromatic aldehyde starting material and the diselenide compound is very important for preparing the desired product, selenyl-substituted aromatic aldehyde compound, with a high yield.

To be specific, when the material having the electron donating substituent was used as the aromatic aldehyde starting material, it was not desirable to use dibenzyldiselenide as the diselenide compound. Instead, dimethyldiselenide or diphenyldiselenide made it possible to obtain the desired product with a high yield.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A selenyl-substituted aromatic aldehyde compound represented by Formula 4:

[Formula 4]

$$\begin{array}{c} R_5 \\ R_6 \diagdown \diagup CHO \\ \diagdown \diagup \\ \diagup \diagdown \\ R_7 \quad A_1 \quad Se\text{—}A \end{array}$$

wherein A is a substitutable $C_{1-10}$-alkyl group, a substitutable $C_{1-10}$-alkoxycarbonyl-$C_{1-10}$-alkyl group, an aromatic cyclic group, a substitutable aromatic cyclic group substituted by one or two of a $C_{1-10}$-alkyl group, a substitutable aromatic cyclic group substituted by a halo group, or a substitutable aromatic cyclic group substituted by a nitro group;

wherein each of the functional groups $R_5$ to $R_7$ is, an aromatic hydrocarbon group, an amine group, a $C_{1-10}$-alkyl group, or a $C_{1-10}$-alkoxy group; and, wherein $A_1$ is N.

* * * * *